United States Patent [19]

Faulconer

[11] Patent Number: 4,607,398
[45] Date of Patent: Aug. 26, 1986

[54] STRAP AND RETAINER FOR A DIVERS MASK

[75] Inventor: Mark Faulconer, Costa Mesa, Calif.
[73] Assignee: U.S.D. Corp, Santa Ana, Calif.
[21] Appl. No.: 633,791
[22] Filed: Jul. 24, 1984
[51] Int. Cl.⁴ ............................................. A61F 9/02
[52] U.S. Cl. ..................................... 2/452; 24/323;
24/585; D2/234
[58] Field of Search ...................... D21/239; D2/234;
2/448–453, 15, 426, 439, 421, 427, 428, 429,
430, 440, 441, 445, 446; 24/16 PB, 191, 196,
585, 170; 351/43

[56] References Cited

U.S. PATENT DOCUMENTS

| | | | |
|---|---|---|---|
| 163,195 | 5/1875 | Hester | 24/191 |
| D. 220,304 | 3/1971 | Wolfe | D2/234 |
| 1,360,360 | 11/1920 | Bigney | 24/191 |
| 2,779,077 | 1/1957 | Kline | D21/239 |
| 3,113,362 | 12/1963 | Petruzziello | 24/585 |
| 3,605,204 | 9/1971 | Amundsen | 2/452 X |
| 4,348,775 | 9/1982 | Haslbeck | 2/452 |
| 4,527,292 | 7/1985 | Kasama et al. | 2/426 X |

FOREIGN PATENT DOCUMENTS 972827  9/1961  United Kingdom ................... 2/448

*Primary Examiner*—Werner H. Schroeder
*Assistant Examiner*—Andrew M. Falik
*Attorney, Agent, or Firm*—George F. Bethel; Patience K. Bethel

[57] ABSTRACT

A strap and retainer for a diver's mask, or other mask to be held on a user's face. The retainer is comprised in part of a molded portion of the frame of the mask with a movable clip portion therein which is pivotally mounted into a molded pocket in the frame of the mask that receives the clip. The clip comprises a main lever portion that is pivotally mounted in the pocket with an angular spring arm portion that rides within the base of the pocket. At the other end of the pivotal lever portion from the spring portion is an angular barb or tooth having a substantially upright angular face portion and a sloping angular face portion. The strap comprises a plurality of ribs, one side of which is substantially normal to the longitudinal relationship of the strap, while the other side has a sloping angular portion which can slide under the tooth of said lever against the sloping angular face portion thereof, while said normal angular face portion is engaged against the upright angular face portion of said lever tooth to block the movement thereof when it is under tension and impressed thereagainst. The strap is connected to the mask frame by a cylindrical transverse roller mounted into the pocket around which the strap is looped.

25 Claims, 7 Drawing Figures

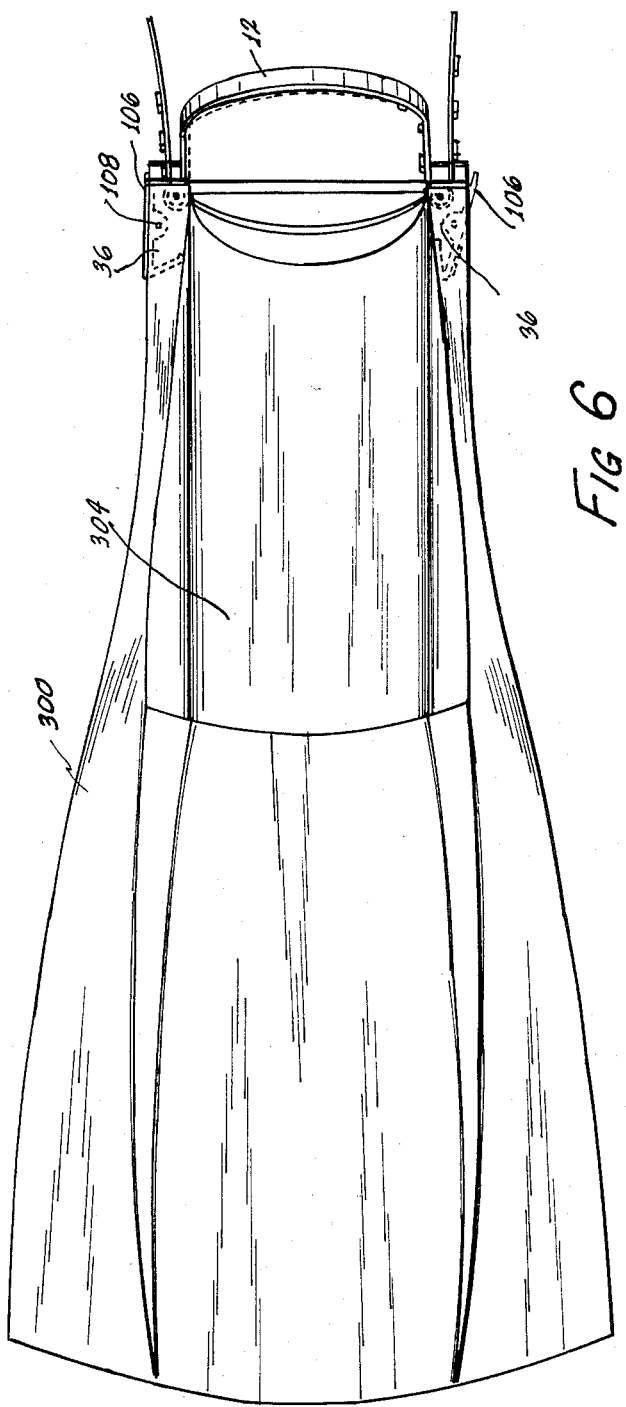
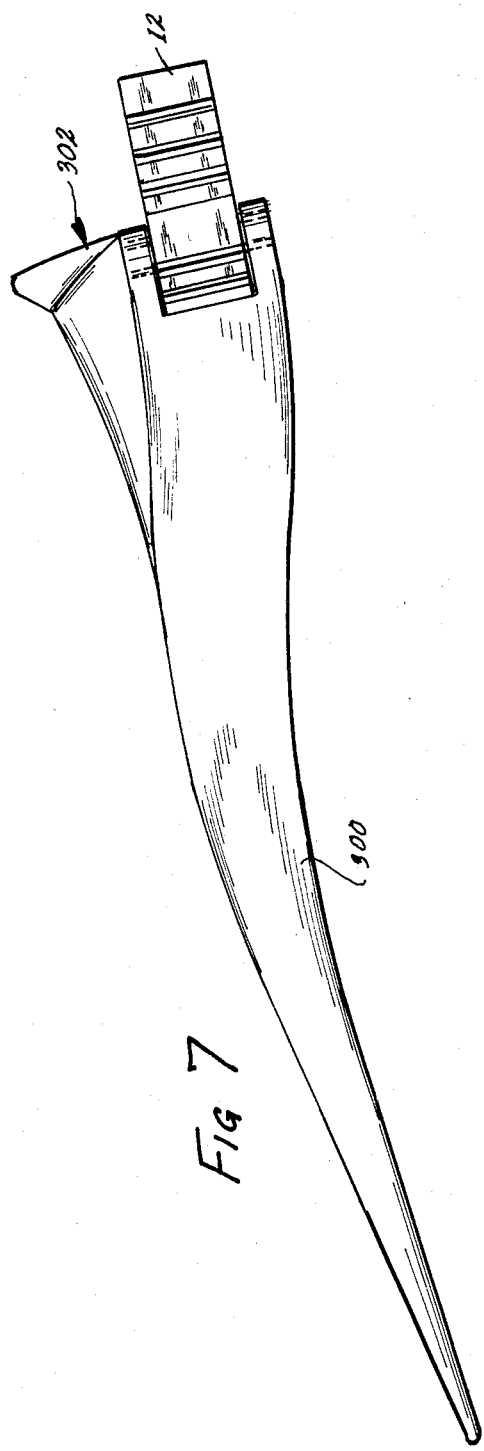

STRAP AND RETAINER FOR A DIVERS MASK

BACKGROUND OF THE INVENTION

1. Field of the Invention

The field of this invention lies within the field of straps, buckles, clips and securement means, as they pertain to retaining a member on one's body. More particularly, the invention pertains to diving equipment, such as masks and fins, wherein the mask and fin is secured to a diver by means of a strap. The strap can be an adjustable strap which can be moved inwardly and outwardly for contraction and expansion thereof for holding a device to a diver's body such as a mask or a fin.

2. The Prior Art

The prior art of straps which are adjustable for divers, and others using self-contained breathing apparatus, whether it be under water or on the surface, includes a myriad of straps, buckles and clip arrangements. For instance, it is well known that harnesses, straps and various types of buckles can be utilized for weight belts, diver's fins, masks, buoyancy compensators and other types of diver's equipment. Also, it is known that self-contained breathing apparatus, for industrial and firemens' equipment, often has harnesses, straps, buckles, cinching frictional engagement clips, connectors, and other devices for holding such equipment in place.

Oftentimes, it is necessary that straps used in the foregoing situations be adjusted. For instance, such straps are used for differently sized people and accordingly need to be adjusted to the user. Various degrees of tension for elastomeric straps are desirable and must be such that they accommodate a user so as to not apply more or less than is desired for a user's comfort.

To this end, the prior art has utilized elastomeric straps for masks. The elastomeric straps for masks sometimes have frictional engagment buckles, or barbed attachment clips. Furthermore, they sometimes have buckles that allow for an over and under passage of the straps in their end to end relationship so that they can frictionally engage each other against the cross members of the buckle.

In addition to the foregoing arrangements, oftentimes straps are utilized with tangs or barbs that specifically engage the strap in an overcenter frictional manner at or near the frame of the mask or fin. It is also known that straps for securement can pass through a convoluted cross bar buckle arrangement to allow for the passage for the strap and at the same time frictional tightening thereof around the cross member.

Accordingly, this invention is directed toward the general area of masks, fins, and other divers' devices as well as self-contained breathing apparatus masks. The general characterization of the invention is that it is such wherein it can be utilized for holding a mask or fin on a user's body with an adjustment which is simple and effective without the need for complex metal buckles, cross members, pivoting barbs and other such means.

The invention solves the problem of mounting a retention means for a strap on a mask or a fin in part by utilizing the frame of the mask or the body of the fin. In particular, this invention has a pocket which is molded into a frame of a mask, or the body of a fin.

The molded pocket portion has support means in the form of walls or brackets which provide for retention of a spring clip therein. The operative aspects of the pocket can be formed with suitable side walls or lateral brackets so that they allow the mounting and support of the spring clip therein and the passage of a loop of a strap therethrough.

The spring clip can be easily mounted in the side walls of the pocket by a pivotal mounting means, such as a pin on which it is journaled. The spring clip can be in the form of a lever member having an elongated barb, tooth or tang at one end having a normal or substantially upright angular face, and on the other side a sloping face. At the other end of the pivotal lever member is a springlike arm, which allows the lever to be sprung into a strap engaging relationship. This is done by the pressure of the spring arm exerting itself against the end of the lever, when impressed against the interior of the pocket.

The body has a cylindrical member therein around which a loop of the strap passes. The loop passes around the cylindrical member and can be frictionally held thereby in some measure or the cylindrical member can be in the form of a roller that is journalled for movement on a pin within the side walls of the body.

The strap has a plurality of transverse ribs on a surface thereof. Each rib is similar to a tooth having a generally upright normal or upstanding angular surface which locks and engages against the angular upright angular surface of the tooth or barb of the lever arm. On the opposite side of the rib from the upright surface is a sloping surface which allows the ribs to pass under a sloping angular portion of the lever tooth so that they can pass by and effectively rachet thereunder against the spring force of the spring arm of the lever.

The foregoing strap and spring clip and pocket arrangement in the frame allows for a mask to have a superior holding means for a strap, whether it be an elastomeric strap or non-stretching strap. It also allows for an integral clip and strap retention means that is not seen in the prior art. As a consequence, the skirt or seal of the mask can be retained in tightened and comfortable juxtaposition to a person's face without undue discomfort. As will be seen, it allows for a facile and easily oriented adjustment by merely pressing against the lever portion and overcoming the spring pressure, or allowing the strap to rachet into adjustment by pulling on the end thereof.

SUMMARY OF THE INVENTION

In summation, this invention comprises a mask for a diver or one using self-contained breathing apparatus which has a frame portion molded with a pocket formed by lateral support walls to receive a spring loaded clip which allows a strap loop to pass therethrough around a transverse member and be retained by said clip.

More particularly, it comprises a diver's mask frame with a pocket formed between lateral wall portions. Inserted in the wall portions is a cylindrical member around which a loop of a strap can pass. The cylindrical member can be a roller so as to provide relatively free movement of the loop of the strap.

Within the pocket walls is a pivoting lever member. The lever member is supported by means of a pin passing therethrough to allow for pivoting movement at either end of the lever. At one end of the lever is a spring arm, which engages an interior surface of the pocket to cause it to be sprung into a position for engagement with the loop of the strap.

The strap has a plurality of ridges or ribs in transverse orientation thereon. Each one of the ribs has a substantially upright or normal face on one side and a sloping face on the other. The sloping face allows for passage of the rib under a barb or tooth having a sloping surface thereof which it engages and passes thereunder, when the strap is pulled at its ends.

Retention of the strap is caused by a substantially upright or normal face of the barb or tooth of the lever member engaging the upright face of the rib or the ridge on the strap. This prevents the rib from passing therethrough until the spring pressure on the lever is overcome to allow for the passage of the rib or ridge thereunder by lifting the respective upright surfaces of the tooth and the rib out of engagement with each other.

The strap can be elastomeric or of any other material having the particular rib or ridges set forth herein so as to allow for adjustment and retention by the spring biased clip. Accordingly, this invention is a new and novel departure over that of the prior art with regard to masks, fins, self-contained breathing apparatus and other related equipment.

BRIEF DESCRIPTION OF THE DRAWINGS

The invention will be more clearly understood by reference to the description below taken in conjunction with the accompanying drawings wherein:

FIG. 6 shows a plan view of the fin of this invention with the strap hereof; and, FIG. 7 shows a side elevation view of the fin with the strap of this invention.

DESCRIPTION OF THE PREFERRED EMBODIMENTS

Figure 1:
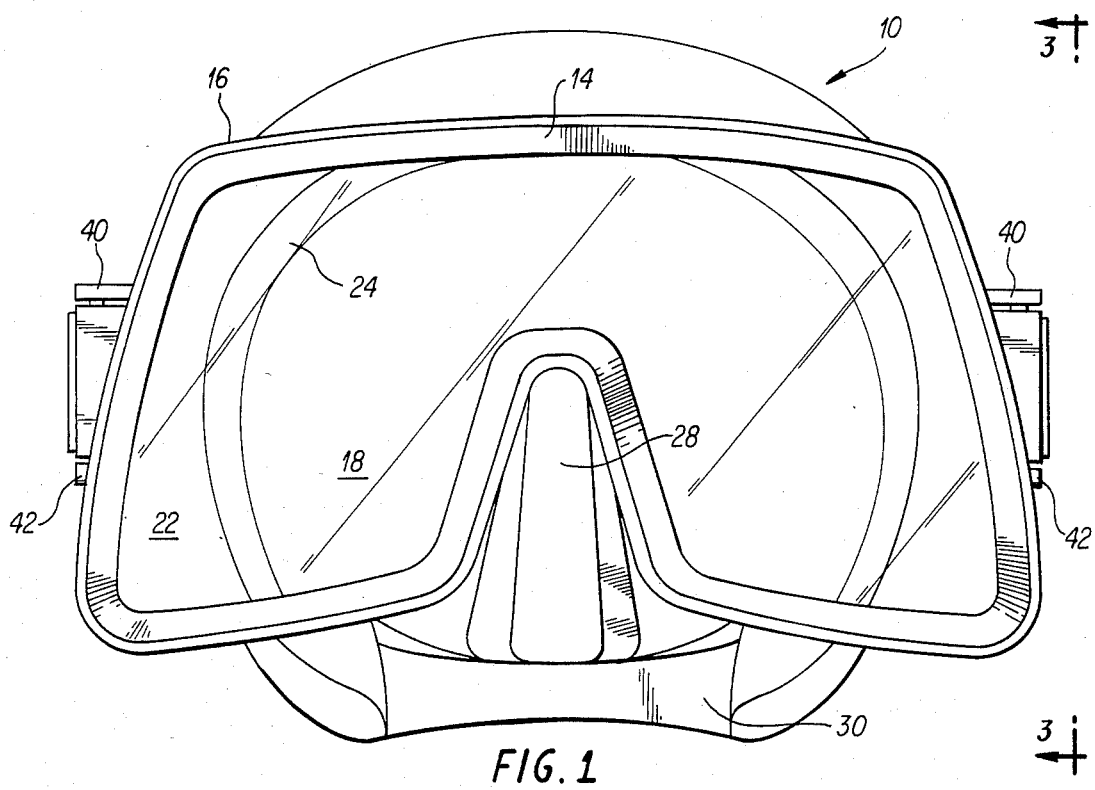
FIG. 1 shows a frontal view of a mask with the spring clip and strap retention means of this invention shown on either side thereof.
Figure 2:
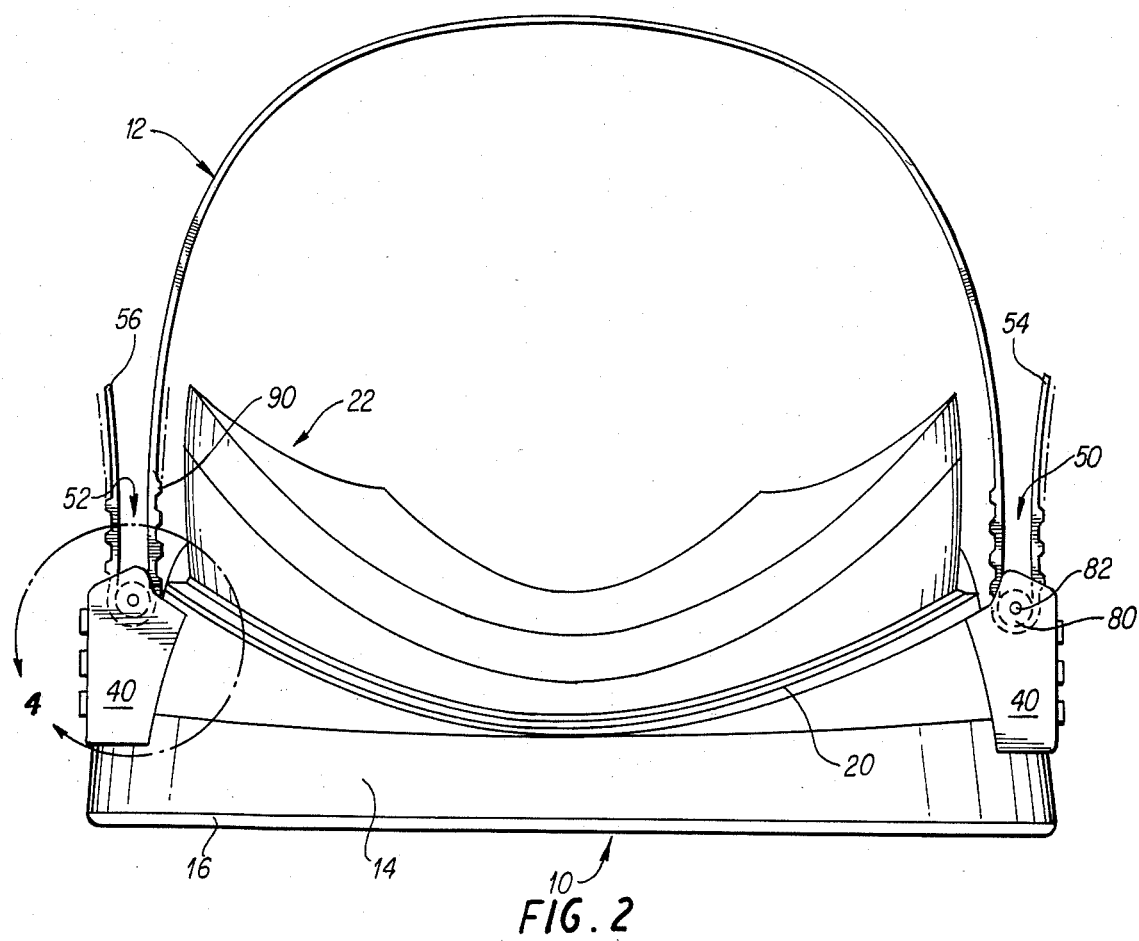
FIG. 2 is a top plan view looking downwardly on the showing of FIG. 1 wherein the mask and the strap are shown in their respective orientations.

Looking particularly at FIGS. 1 and 2, it can be seen that a mask 10 has been shown. The mask 10 is secured to a user's head by means of a strap 12. The mask 10 includes a frame portion 14 with a viewing port having a bezel 16 or mounting means for a transparent lens such as glass or plastic 18 implaced therein. The bezel can be formed with a metal strap and elastomeric seal to seal the lens 18 in the viewing port area. The frame 14 can be molded in any suitable manner to provide for a facial contour.

In the particular embodiment shown herein the frame 14 has a curved frame portion 20 which follows a generally smooth contour. Within the arcuately curved portion 20 is a retention or receipt area for an elastomeric skirt 22. The elastomeric skirt 22 extends backwardly into a seal area 24 which allows the mask to seal against a diver's face.

Generally, the seal area 24 follows the general contour of a user's face and has a doubled back flared flap portion which seals against a user's face in conjunction with the skirt 22. Of course, the skirt 22 can be of any suitable configuration to adapt itself to a user's face. To this extent, the skirt 22 has a nose receipt area 28 which receives a diver's nose so as to allow for a seal against a diver's nose with a lower lip 30 which forms a portion of the skirt 22 and seal 24.

All the foregoing general configurations for a mask are generally seen in the prior art. In particular, frame 14 with the bezel 16 are known. Such frames can be in the form of plastic molded frames or metal frames, wherein a metal band is substituted for the frame 14 and bezel 16. In such forms, a metal band circumscribes a round or oval piece of glass substituted for the glass 18. In such a manner the mask can be provided with a bezel and frame formed generally with a skirt 22 which overrides a glass portion with a metal band or bezel portion circumscribing the elastomeric material securing it thereto.

Suffice it to say, the mask and frame of this invention can have various configurations. However, the frames to be utilized with the mask of this invention preferably has a portion of the retention means of this invention molded therein.

Figure 3:
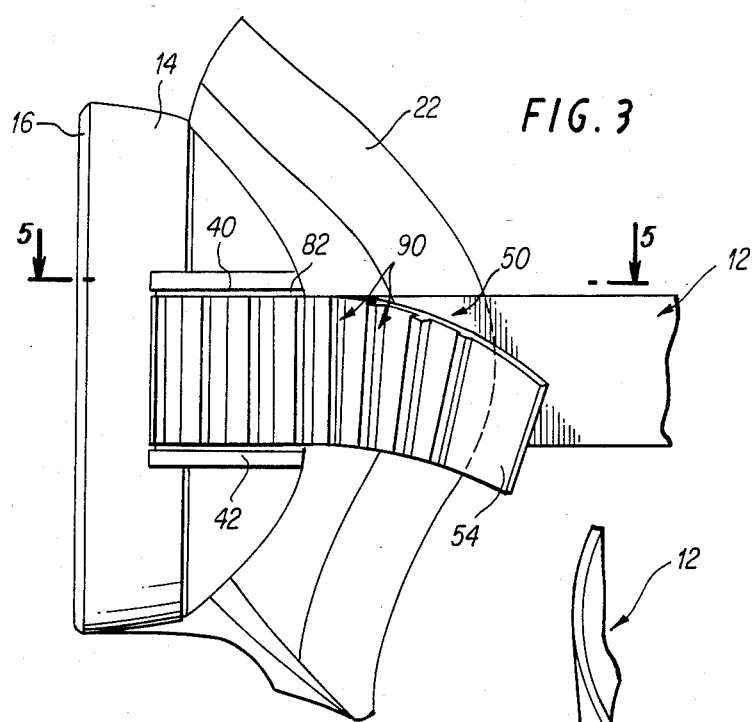
FIG. 3 is a side view looking in the direction of line 3—3 of FIG. 1.
Figure 4:
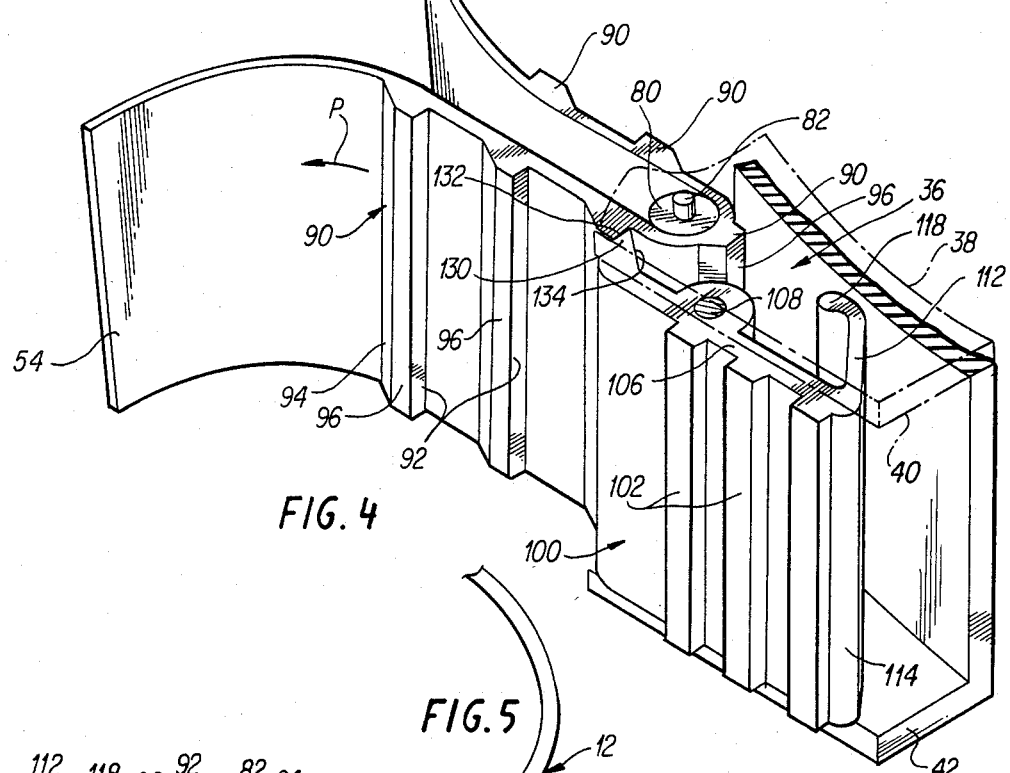
FIG. 4 is a partially broken away and fragmented view of the area encircled by circle 4 of FIG. 2, with a portion of the frame and pocket walls in dotted configuration; and, FIG. 5 is a sectional view looking downwardly in the direction of lines 5—5 of FIG. 3.

Looking more particularly at the frame 14, it can be seen that a pocket area as shown in FIG. 4, namely pocket area 36 has been molded into the side of the frame area 38. The pocket portion 36 and the frame area 38 have an upper and lower wall portion, respectively 40 and 42 forming the pocket area 36. The upper and lower wall portions 40 and 42 are seen in the two respective sides of the mask in a frontal view of FIG. 1, a top view of FIG. 2 and the detailed views of FIGS. 3 through 5. The wall portions 40 and 42 are in effect lateral brackets extending from the frame portion 38.

Looking more particularly at the frame area portion 38 adjacent the pocket 36, it can be seen that it is formed or molded on the left and right side of the mask and are mirror images respectively on each side of the mask. Accordingly, the description pertaining to one side of the mask as to the invention will be analogous to the other side of the mask which receives and retains the strap as detailed hereinafter.

Looking at the strap 12, it can be seen that it has loops generally shown as loops 50 and 52. Loops 50 and 52 terminate in end portions respectively 54 and 56 so that the strap 12 can be adjusted at the ends 54 and 56 by pulling the ends and adjusting the intermediate portions of the strap 12 around a diver's head.

The pocket 36 with the frame portions 38 at the base thereof is inset into frame 14 in any suitable manner. Inasmuch as the strap and retainer hereof can be used for purposes other than a diving mask, the pocket 38 can be inset into the body of a swim fin, or self-contained breathing apparatus mask for an industrial worker or fireman. When used with a swim fin, brackets 40 and 42 with pocket 36 are molded into the side body wall of a fin. Regardless of the foregoing, the pocket 36 can also be formed as a separate portion that is not integral with the frame 14. In other words, the frame 14 can be manufactured in a manner whereby the pocket portion 36 with the walls 40 and 42 can be provided as separate attachment or support means to be connected to the frame in any suitable manner. They can also be formed as side bracket members or extensions from the frame 14. Attachment means, of course can be in the form of bonding, welding, adhesives, rivets, or any other means.

Preferably, the frame 14 is molded of a plastic. The molding process can be an injection molding process or any other suitable process for forming a frame. During the molding process of the frame 14, the pocket 36 is molded therein to include the laterally extending walls, supports or lateral brackets 40 and 42 which form the upper and lower wall portions of the pocket.

The upper and lower wall portions 40 and 42 can be configured in any kind of shaped brackets or extending members. In effect, the wall portions 40 and 42 can be formed as rounded or rectangular brackets to extend from the side of the frame 14 as in the form of ears.

Looking more particularly at FIG. 1 and the frontal view thereof, it can be seen that the wall portions 40 and 42 extend from the frame 14 in the form of ears so as to create a pocket therebetween or a space for receipt of the operative aspects of this invention.

Turning to FIGS. 3, 4 and 5 again, it can be seen that the pocket 36 with the walls 40 and 42 receive a cylindrical member 80 therein. The cylindrical member 80 is journaled for rotation about an axis provided by a pin 82 in the walls or support brackets 40 and 24. The pin 82 is such wherein it can cause the cylinder 80 or roller to turn therearound.

The rotational movement of the roller 80 around the pin 82 can be provided in any other suitable manner, such as by members having different cross sections other than roller 80. For instance, eliptical rollers or rectangular rollers can provide different functions and results. Furthermore, roller 80 can be molded integrally into the extending side walls or brackets 40 and 42 as a non-movable roller without the pin 82 upon which it is journaled. In effect, it can be any transverse member. In such a manner it would provide more frictional engagement of the loops 50 and 52 but would nevertheless serve its function.

In addition to the foregoing, the roller or cylinder 80 can be substituted with any suitable fixed configuration or cross section which can allow the loops 50 and 52 to pass therearound in a manner set forth hereinafter.

Looking more particularly at the strap 12 which passes around the roller 80, it can be seen that a plurality of ribs, ridges or teeth 90 have been shown. The ribs, ridges or teeth 90 form a plurality of transverse members across the strap 12. The transverse members 90 can fully cross the strap or be segmented or formed in any suitable manner so long as they provide the checking and retaining function set forth.

The transverse members or ridges 90 have an upstanding or relatively upright face 92 which is on one side of the ridge, which forms the trailing portion of the ridge 90 as it is passing through the pocket 36 when the strap is to be cinched up or tightened by pulling the ends 54 or 56. On the reverse side of the ridge 90, from the side 92 is a sloping surface 94 in the form of an angular sloping surface which slopes away from the crown 96 of the ridge downwardly toward the major surface of the strap.

The crown 96 of the ridge can be round or in this particular case a flattened area. Regardless of the foregoing, it is preferable to have a substantially upright, normal, or angularly vertical surface 92 extending from the longitudinal relationship of the strap to the crown 96. On the other side of the crown, a sloping surface 94 is provided. The foregoing configuration of the rides 90 of the strap will be expanded upon as to their function.

Figure 5:
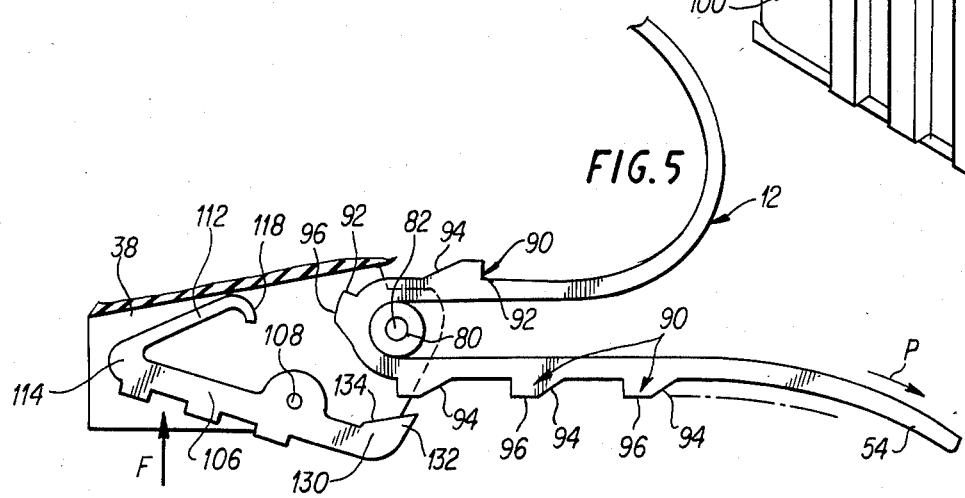

Looking more particularly at FIGS. 4 and 5 it can be seen wherein a clip 100 is shown having a plurality of ridges 102. The plurality of ridges 102 are for a finger grip as will be set forth hereinafter.

The clip 100 comprises a main lever or arm portion 106. The main lever portion 106 is pivotally mounted around a pin 108 which is implaced within openings of the upper and lower walls 40 and 42. Thus, the lever 106 is allowed to move in a pivotal manner backwardly and forwardly around the axis of the pin 108.

The lever 106 has a spring arm 112 connected thereto at an angle portion 114. The angle portion 114 has been shown as a rounded edge. In addition thereto, a rounded arcuate surface 118 is shown which extends from the end of the spring arm 112. This round upwardly extending bearing surface 118 allows for impingement against the interior surface of the pocket and frame portion 38 for smooth sliding thereover. The rounded upwardly extending portion 118 can be substituted by any protuberance, bulbous, or rounded end to prevent unwarranted engagement by spring arm 118.

Looking more particularly at the lever arm 106 it can be seen that at the end opposite from the curve 114, is a barb, tang, or elongated tooth 130. The elongated tooth 130 has a substantially upright portion 132 and a sloping portion 134. The sloping portion 134 and the upright portion 132 interact with the ridges of the strap in the manner as can be seen within the two respective articulated movements as shown in FIGS. 4 and 5.

In particular, looking at FIG. 4, it can be seen that the strap 12 is engaged with an upright surface 92 thereof against an upright surface 132 of the barb, tang or tooth 130. This is due to the fact that the mask strap 12 is under tension usually when it is secured to a user's head and accordingly engages the two respective surfaces 132 and 92.

These two upright surfaces with the tooth engaging the surface 92 causes a tightened clamping of the strap 12 so that it is relatively immobilized. This in great measure is due to the fact that the tooth surface 132 engages the upright surface 92 of the strap, and is in close juxtaposition to an underlying surface, namely roller 80. However, any particular surface other than roller 80 can be utilized to allow the tooth 130 to engage the strap 12 between the roller 80 and the tooth 130. Thus, it is not necessary that the specific roller engagement is shown herein be utilized as being the underlying surface against which the tooth 130 is sprung against. The necessary criteria for locking engagement is that the elastomeric nature of strap 12 not cause the strap to collapse under the engagement of tooth 130.

Looking more particularly at the spring arm 112, it can be seen that it engages the interior surface 38 of the pocket by means of an upright arcuate curve portion 118 engaging it. The foregoing upright surface or arcuate portion 118 can be of any suitable non-binding member, as previously stated, such as a round protuberance, bulbous portion, or other rounded surface.

The foregoing spring arm 112 is shown in a bent position with the lever 106 sprung downwardly through force in the direction of arrow F. The force in the direction of arrow F is provided by hand articulation or movement in order to cause a disengagement of the tooth 130 of the strap 12.

The strap 12 when disengaged by the tooth 130 as shown in FIG. 5 is free to move due to the fact that the upright surface 132 no longer engages the upright portion of the ridge 90, namely upright portion 92.

As can be appreciated, when the strap is pulled at the free end, such as free end 56 in the direction of arrow P (for pull and tighten), it causes the sloping surface 94 to engage the sloping surface 134 of the tooth. This allows the strap 12 to travel around the roller 80 underneath the lever arm so that it toggles backwardly and forwardly under the spring pressure of spring arm 112.

Thus, adjustment or tightening around one's head or when this device is used for a swim fin can be accommodated by pulling the strap 12 in the direction of arrow P. This causes the surfaces 94 of ridges or ribs 90 to engage the tooth surface 134 and thereby pass them by the lever arm articulating backwardly against the pressure of spring lever member 112. In effect, surfaces 94 engaging tooth surface 134 toggle the lever 106 until it is seated again with the surface 132 thereof against surface 92 for locking of the strap 12.

As can be seen from the foregoing, the strap 12 is adjustable in the direction of arrow P for purposes of tightening the strap by pulling on ends 54 and 56. The force and articulated movement in the direction of arrow F allows the release of the tooth 132 against the surfaces 92 so as to allow the strap to pass around the roller 80 and be loosened. This can be accomplished by pulling the strap at the intermediate portion thereof or allowing the elasticity thereof to be released as to its tension, when lever 100 is pushed in the direction of arrow F.

It should be understood that the articulated showing of FIG. 5 is such wherein the strap is either being pulled in the direction of arrow P such that it causes a movement under the tooth 130 by the sloping surface 94 pushing surface 134, or due to a force F which has actually been imposed against the force of spring arm 112 to lift the tooth 130 over the ridges or ribs 90. In either manner, the strap 12 is allowed to slip by the ratchet surface of the vertical or upright portion 132 of the tooth by not engaging the upright portion 92 of the rib 90.

FIG. 6 shows a fin 300. The fin 300 has a foot pocket 302 which receives a foot within the area 304. The fin 300 is such wherein said pockets 36 have been provided on either side with the analogous walls 40 and 42. The side pockets 36 have the spring clip member or lever 106 connected thereto through the pin 108 as shown for actuation and movement analogous to the previous showing in the mask. Thus, the strap 12 can be adjusted in the same manner as previously described. In particular, FIG. 6 shows the lever 106 pushed inwardly to release the strap 12 while on the other side the lever is engaging the strap.

This invention allows for adjustment of a strap for a mask or fin such as that shown when the pocket 36 with brackets or walls 40 and 42 have been molded into the frame or side body wall of a fin to which the strap 12 is to be attached. Also, it should be noted that the entire clip 100 can be formed of a highly resistant resilient plastic such as Delrin, or any other suitable plastic. It can also be formed as a metal member that is stamped, cast or molded in any suitable manner. However, it is believed that inasmuch as the device will often be used in the water, that it is preferable that the clip 100 be molded of plastic and the pins 82 and 108 to be formed of stainless steel, with the remaining portions of the elastomer of the strap 90 and frame 14 being formed of non-corrosive material, such as rubber and plastic. Accordingly, this invention should be read broadly in light of the following claims.

I claim:

1. A strap and retainer for use in securing an object to a user's body comprising:

a body portion of an object that is to be secured to a person's body;

support means extending from said body portion having a space therebetween;

a lever member pivotally connected within the space of said support means;

spring means at one end of said lever member for engaging a portion of an interior surface of the space between said support means;

tooth means distally disposed from said spring means wherein said tooth means have a first upright surface and a sloping surface extending therefrom;

means extending between said support means around which said strap can be looped;

ribs on said strap having an upright portion and a sloping portion on either side of said ribs, such that said sloping portion can engage said sloping portion of said tooth means and the upright portion can engage the upright portion of the tooth means of said lever arm under the spring pressure of said spring means; and, wherein said ribs and said tooth means can be mutually caused to pass each other by movement of said respective sloping surfaces of said strap and ribs passing against each other, and said tooth means of said lever arm disengaging the upright portion of said rib by movement against the force of said spring means.

2. The strap and retainer as claimed in claim 1 wherein:

said support means extend from said body and provide a pocket into which said lever arm can be moved.

3. The strap and retainer as claimed in claim 2 wherein:

said support means extending from said body comprises brackets formed as a portion of said body.

4. The strap and retainer as claimed in claim 2 further comprising:

two wall portions forming said support means extending from said body with a pocket therebetween; and wherein, said body forms at least a portion of a frame of a diver's mask.

5. The strap and retainer as claimed in claim 4 wherein:

said means around which said strap is looped is formed as a cylindrical member.

6. The strap and retainer as claimed in claim 5 wherein:

said cylindrical member around which said strap is looped is a rotatable roller journaled on a pin extending into said two wall portions extending from said frame.

7. The strap and retainer as claimed in claim 6 wherein:

said lever is pivotally mounted on a pin extending into said two wall portions extending from said frame and which provide a pocket into which said lever can be placed;

and wherein said spring means comprises an angular arm depending into said pocket between said wall portions extending therefrom and having a rounded end of said spring arm for engagement against an interior surface of said pocket for allowing it to move thereacross when said spring arm is flexed by said lever arm being articulated.

8. The strap and retainer as claimed in claim 7 wherein:
said tooth in distal relationship from said spring arm has an upright tooth surface and a sloping surface thereof which substantially correspond in slope and degree of upright orientation to the surfaces of said ribs.

9. The strap and retainer as claimed in claim 8 wherein:
said strap is formed of an elastomeric material, and said lever arm is formed of a molded plastic material.

10. The strap and retainer as claimed in claim 9 further comprising:
relieved surface portions of said lever arm for impressment by a user's finger so as to allow one to engage and press down on said lever arm against a relieved surface.

11. A mask for a diver having a viewing port and a seal with a strap to hold the mask on a user's head comprising:
a frame portion that is formed with a viewing port therethrough;
means on said frame for receiving a transparent lens within said viewing port for providing viewing by a diver;
a skirt surrounding said frame with a seal thereon for being received against a diver's face and sealing the interior of the mask;
clip support means extending from the two respective sides of said mask having a space therebetween;
a clip member pivotally mounted between said support means;
tooth means on said clip member having a substantially upright surface on the face of the tooth and a sloping surface on the opposite face of the tooth;
spring means for providing spring bias to said clip means for causing said tooth to move in the direction of its end;
a strap having ribs thereon with a substantially upright face and a sloping face opposite therefrom;
means for supporting a loop of said strap between said clip member support means so that as said tooth engages a substantially upright surface of said rib with a matching upright surface it can block movement thereof by the spring bias of the clip against said tooth while permitting movement of said strap by said sloping face of said strap sliding against said sloping surface of said tooth against said spring bias.

12. The mask as claimed in claim 11 wherein:
said clip member comprises a pivotally mounted lever.

13. The mask as claimed in claim 12 further comprising:
spring means attached to said pivotally mounted lever that is integral therewith for providing the spring bias to the clip; and wherein
the support means are formed on the frame of the mask by two extending walls providing a space therebetween into which said clip member can be articulated inwardly at the spring end of said clip member.

14. The mask as claimed in claim 13 further comprising:
a transverse member supported between the walls extending from said frame around which said strap can be looped forming said loop support means; and,
wherein said transverse member receives the pressure exerted at the tooth of said spring clip thereagainst.

15. The mask as claimed in claim 14 wherein:
said transverse member comprises a roller that is rotationally journaled for movement between said two extending walls.

16. The mask as claimed in claim 15 further comprising:
a relieved surface on said lever proximate to said spring means to provide for manual depression of said clip against said spring means.

17. A swimming fin with a strap for use therewith comprising:
a swimming fin having a pocket for receipt of a user's foot;
spaced support wall means extending from each side of said wall on each side of said user's foot pocket;
a spring clip supported between each of said spaced wall means wherein said spring clip has a pivotal support between said support wall means and comprises a lever with a spring member at one end and a tooth at the other end wherein said spring member engages said wall of said fin;
a transverse member extending between said spaced support wall means around which a loop of a strap can be looped;
transverse rib means on said strap having a substantially upright surface and a sloping surface on the other side of said rib; and wherein,
said tooth has an upright surface and a sloping surface thereof wherein said upright surface causes said upright surface of said ribs to be checked thereby and said sloping surface allows the sloping surface of said ribs to pass thereunder when said clip member is depressed so as to disengage itself or when said strap is pulled with said sloping surfaces of said ribs and tooth moving in mutually passing relationship to each other against the force of said spring clip.

18. The fin as claimed in claim 17 wherein:
said spring clip is molded from a single piece of plastic; and,
said spring means comprise an end extending from said lever in a slanted relationship toward said pivotal mounting of said spring clip and engages the side wall of said fin.

19. The fin as claimed in claim 18 further comprising:
rounded end means for said spring means engaging said wall of said fin to prevent binding thereof.

20. The fin as claimed in claim 19 wherein:
said transverse support means around which said strap passes is formed as a roller for providing friction free movement of said strap.

21. A mask for a diver in combination with a strap wherein said mask is formed with a frame member having an opening passing therethrough to provide a diver's viewing port with a transparent lens implaced within said frame member overlying said port and a skirt and seal portion extending from said frame portion for engagement with a user's face wherein said strap and retainer means comprise:
a strap having a plurality of transverse ribs thereon wherein said ribs have a substantially upright surface and a sloping surface in opposite relationship to said upright surface so as to provide a substantially upright surface and a sloping surface for said ribs terminating in a crown;

at least two support members extending from said frame comprising bracket walls from the side of the frame;

a clip member for providing retention of said strap formed as a pivoting lever member pivotally journaled between said bracket wall members extending from said frame wherein at one end of said lever a tooth is provided having a substantially upright surface terminating in a crown and a slanting surface from said crown opposite from said upright surface;

spring means extending from said lever member in distal relationship from said tooth member on said lever member for biasing said lever member;

transverse strap support means extending between said bracket walls for providing a holding member around which a loop of said strap can be oriented for holding it therein so that as said loop is passed therearound, the upright surfaces of said strap ribs can engage the upright surface of said tooth and be held therein by spring bias of said spring means of said lever; and, wherein said lever means and said tooth means and said spring means are formed as a single plastic molded item.

22. The combination as claimed in claim 21 wherein: said support member bracket walls are integrally formed as a plastic molded item with said frame.

23. The combination as claimed in claim 22 wherein: said transverse member extending between said support member bracket walls comprise a roller journaled therein.

24. The combination as claimed in claim 23 wherein: said spring means connected to said lever arm means comprise a slanting angular spring member integrally formed therewith having a rounded end thereof which engages the frame portion between said support member bracket walls supporting said clip member.

25. The combination as claimed in claim 24 further comprising:

a relieved surface on said lever means in overlying relationship to said spring means for allowing said spring to be depressed by manual articulation for causing said tooth means to lift over said ribs by depression thereof when it is depressed so that when the upright portions of the rib means engage the upright portions of said tooth, the strap will be locked, yet when said strap is moved with the respective sloping surface of said rib means engaging said sloping surface of said tooth means, it will cause said lever arm to move pivotally against said spring means.

* * * * *